United States Patent [19]

Matumura et al.

[11] Patent Number: 5,636,256
[45] Date of Patent: Jun. 3, 1997

[54] APPARATUS USED FOR TOTAL REFLECTION FLUORESCENT X-RAY ANALYSIS ON A LIQUID DROP-LIKE SAMPLE CONTAINING VERY SMALL AMOUNTS OF IMPURITIES

[75] Inventors: Tuyoshi Matumura, Kawasaki; Kunihiro Miyazaki, Tokyo; Hisashi Muraoka, Yokohama, all of Japan

[73] Assignees: Kabushiki Kaisha Toshiba, Kawasaka; Purex Co., Ltd., Yokohama, both of Japan

[21] Appl. No.: 706,363

[22] Filed: Aug. 30, 1996

Related U.S. Application Data

[63] Continuation of Ser. No. 427,910, Apr. 26, 1995, abandoned.

[30] Foreign Application Priority Data

Apr. 27, 1994 [JP] Japan .................................. 6-090086

[51] Int. Cl.$^6$ .................................. G01N 23/223
[52] U.S. Cl. .................................. 378/45; 378/79
[58] Field of Search .................................. 378/44, 45, 79

[56] References Cited

FOREIGN PATENT DOCUMENTS 49-115391  11/1974  Japan .................................. 378/45

OTHER PUBLICATIONS

"Total Reflection X-Ray Fluorescence Analysis for Ultratrace Surface Contamination", K. Miyazaki et al., Technical Report of IEICE, pp. 7–12 (1994).

*Primary Examiner*—Craig E. Church
*Attorney, Agent, or Firm*—Finnegan, Henderson, Farabow, Garrett & Dunner, L.L.P.

[57] ABSTRACT

An apparatus is disclosed which is used for total reflection fluorescent X-ray analysis on a liquid drop-like sample containing very small amounts of impurities. The apparatus comprises a heat-resistant thin sheet containing an element or elements, as a principal component, not detected on total reflection fluorescent X-ray analysis and an x-ray source directing an X-ray as an incident X-ray at a liquid drop-like sample put on the sheet and containing very small amounts of impurities whereby the liquid drop-like sample is evaporated to a dried solid for the total reflection fluorescent X-ray analysis to be performed there.

10 Claims, 2 Drawing Sheets

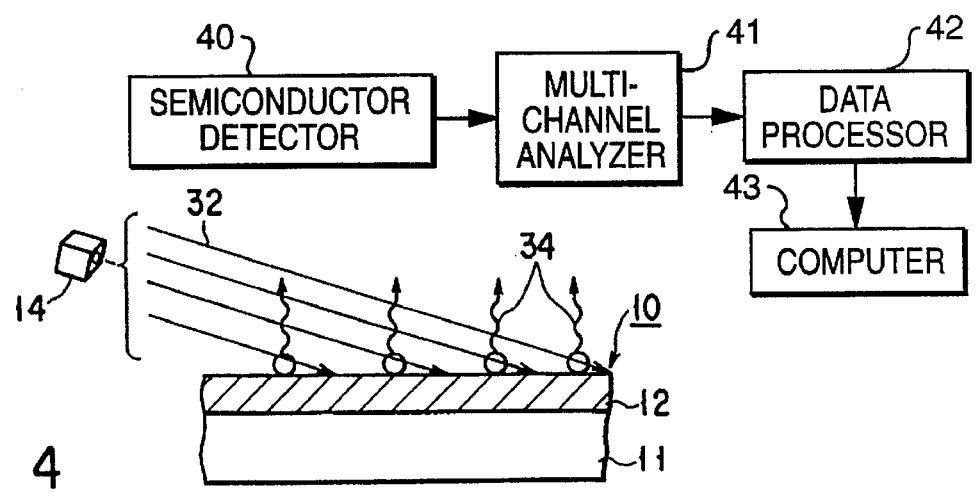
F I G. 4
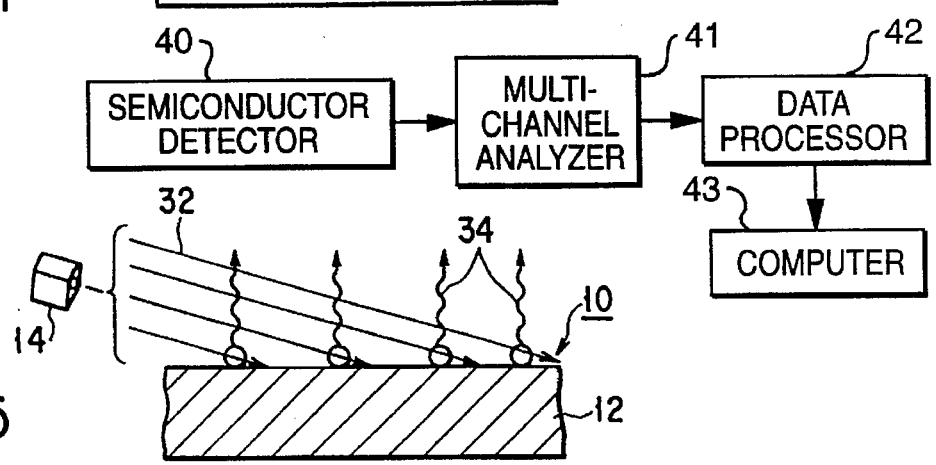
F I G. 5
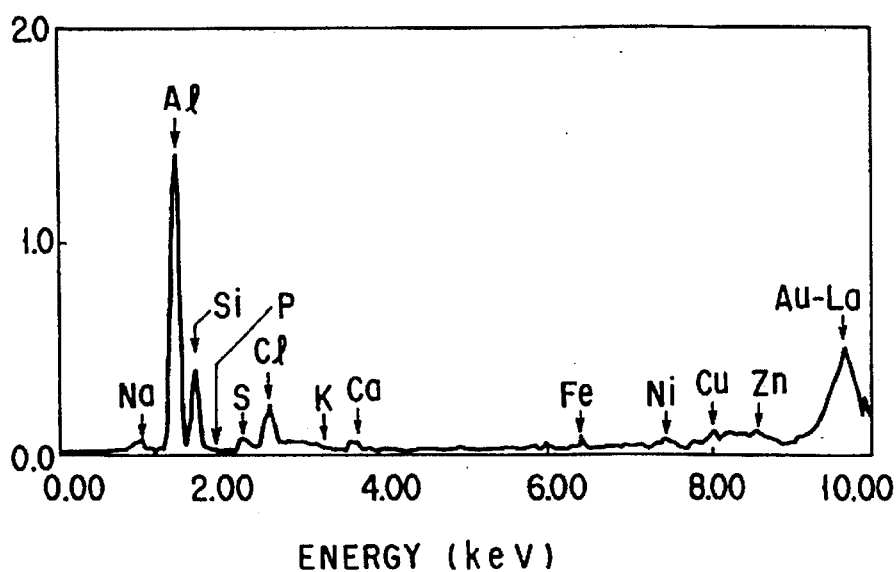
F I G. 6

APPARATUS USED FOR TOTAL REFLECTION FLUORESCENT X-RAY ANALYSIS ON A LIQUID DROP-LIKE SAMPLE CONTAINING VERY SMALL AMOUNTS OF IMPURITIES

This application is a continuation of application Ser. No. 08/427,910, filed Apr. 26, 1995, now abandoned.

BACKGROUND OF THE INVENTION

1. Field of the Invention

The present invention relates to an apparatus used for analyzing very small amounts of impurities, by total reflection fluorescent X-ray analysis, which are collected as a liquid drop on a sheet, in particular, on a semiconductor wafer.

2. Description of the Related Art

An apparatus using a fluorescent X-ray analysis method has been known as an apparatus for analyzing very small amounts of impurities deposited on a sheet. As the sheet, use is made of a quartz, a silicon, a plastic, and etc., sheet. Here, explanation will be given below, by way of example, about analyzing very small amounts of impurities deposited on a semiconductor wafer in particular.

As shown in FIG. 1, for example, upon the falling of an incident X-ray 32 on a silicon wafer 31 as a semiconductor wafer, a fluorescent X-ray 34 is produced from impurities 33 deposited on the silicon wafer 31. It is possible to identify elements from the wavelengths of the fluorescent X-ray 34 and to analyze amounts of elements from the intensities of the fluorescent X-ray. It is, therefore, possible to detect the number of atoms/cm$^2$ in the impurity elements involved. The angle of incidence, $\phi$, of the incident X-ray 32 is greater than the so-called total reflection critical angle $\phi$ crit, that is, the angle of incidence at which a "total reflection" phenomenon occurs. The incident X-ray 32 penetrates into the interior of the silicon wafer 31 so that a fluorescent X-ray is produced from the silicon wafer 31 per se. In such a conventional fluorescent X-ray analysis method, there is a drawback in that signal noise is produced from that base material due to the X-ray involved and the so-called background emerges at an increasing level.

As a solution to this problem, a total reflection fluorescent X-ray analysis method as shown in FIG. 2 is known.

According to this method, an angle of incidence, $\phi$, of the incident X-ray 32 is made smaller than that used conventionally and, without penetrating into the silicon wafer 31, the incident X-ray is totally reflected on that surface. The incidence angle $\phi$ at this time is lower than the total reflection critical angle $\phi$ crit. This total reflection critical angle $\phi$ crit, though varying in the situations involved, is about below 1°.

The fluorescent X-ray reflected on the surface of the silicon wafer 31 in a 18 to 20 mm range is detected by a semiconductor detector. In this case, the normal impurity detection sensitivity E is about E=10 atoms/cm$^2$. The semiconductor detector is fixed just over the surface of the silicon wafer 31. According to this method, it is possible to suppress the scattering of the incident X-ray and the rise of background by the fluorescent X-ray from the base material and hence to achieve high-sensitivity analysis.

When higher sensitivity analysis is required, the above-mentioned total reflection X-ray analysis method has conventionally been performed after the treatment of the silicon wafer surface with a hydrofluoric acid.

First, metal impurities deposited on the silicon wafer surface are decomposed with a hydrofluoric acid gas, a diluted hydrofluoric acid drop is scanned, as a liquid drop, on the surface to collect the metal impurities into the liquid drop, and the liquid drop is put on another silicon wafer surface to allow the water content of the liquid drop to be evaporated so that the metal impurities are dried to a solid. The solid thus obtained is analyzed by the total reflection fluorescent X-ray analysis method. According to this method, it is possible to provide a greater ratio between an analytical area and a dried solid area of the liquid drop and hence to improve the analytical sensitivity.

According to any above-mentioned methods, the fluorescent X-ray of silicon emerges as a main peak from the basic material as shown in FIG. 3. FIG. 3 shows how the intensity of the fluorescent X-ray reflected differs from element to element. That is, the number of X-ray detected during a time period of t seconds is represented by a cts unit.

An energy-distributed type semiconductor detector is used as high-sensitivity total reflection fluorescent X-ray detector but its energy resolution is of the order of one hundred and several tens of eV. When, therefore, a large peak of silicon emerges at 1.7 KeV, it is not possible to analyze the elements aluminum (Al) and phosphorus (P) because the intensity peaks of fluorescent X-rays of these elements Al and P overlap with that of silicon whose energy position is located 0.25 KeV away from that of Al and 0.27 KeV away from that of P. Further, due to the level of an S/N ratio involved, a rise in the intensity peak of the Si fluorescent X-ray leads to a rise in background of other impurity metals, so that it is difficult to achieve high-sensitivity analysis.

In contrast, attempts have been made to conduct analysis by coating an amorphous fluorine resin as a thin film on a silicon wafer and, putting a metal impurity-containing "liquid drop" on the coated silicon wafer, evaporating the water content of the liquid drop to a dried solid.

However, the thin film coated surface of the silicon wafer is liable to be degenerated through a thermal reaction with active chemicals, these being a risk that no requisite flatness will be obtained on total reflection fluorescent X-ray analysis. Further, the degeneration of the surface leads to poor heat conduction and a dried solid configuration of any liquid drop exhibits poor reproducibility on the surface. As appreciated from the above, difficulty has been encountered in the high-sensitivity analysis of the metal impurity on the thin film coated with the amorphous fluorine resin.

SUMMARY OF THE INVENTION

It is accordingly the object of the present invention to provide an apparatus used for total reflection fluorescent X-ray analysis on a liquid drop-like sample containing very small amounts of impurities, which can suppress the generation of fluorescent X-ray energy from a sheet itself, upon illumination of the sample with an X-ray, and can detect not only Si (silicon) in very small amounts of impurities but also those light elements, such as Na, Al and P.

In order to achieve the above-mentioned object of the present invention, there is provided an apparatus comprising sheet means made of a heat-resistant thin sheet containing, as a principal element, an element or elements not detected by the total reflection fluorescent x-ray analysis and an X-ray source directing, as an incident X-ray, an X-ray at a liquid drop-like sample put on the sheet means and containing very small amounts of impurities.

The apparatus of the present invention as set out above is used for total reflection fluorescent X-ray analysis on the liquid drop-like sample containing very small amounts of impurities and can suppress the generation of an X-ray energy from the sheet means itself and very accurately can detect not only Si (silicon) in the very small amount of impurities but also those light elements, such as Na, Al and P.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a cross-sectional view showing a sheet of an apparatus according to one embodiment of the present invention;

FIG. 5 is a cross-sectional view showing a sheet of an apparatus according to another embodiment of the present invention; and FIG. 6 is a view showing a result of analysis obtained by total reflection fluorescent X-ray analysis on a a dried solid to which a liquid drop containing very small amounts of impurities is evaporated on the sheet, the result of analysis showing the intensities of those different impurities involved.

DETAILED DESCRIPTION OF THE PREFERRED EMBODIMENTS

Figure 1:
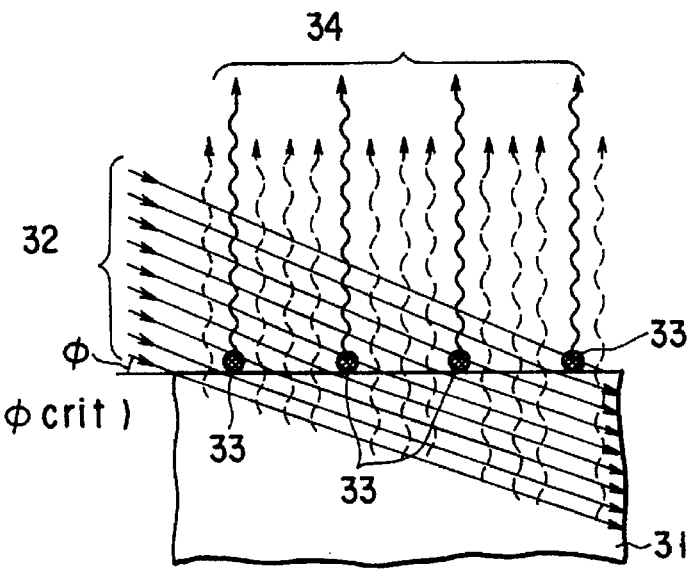
FIG. 1 is an explanatory view for explaining a conventional method for performing fluorescent X-ray analysis.
Figure 2:
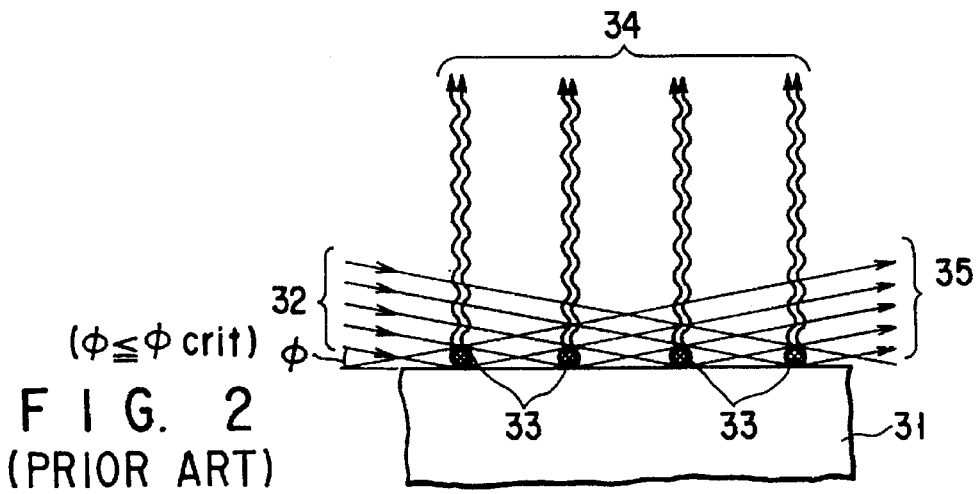
FIG. 2 is an explanatory view for explaining a conventional method for performing total reflection fluorescent X-ray analysis.
Figure 3:
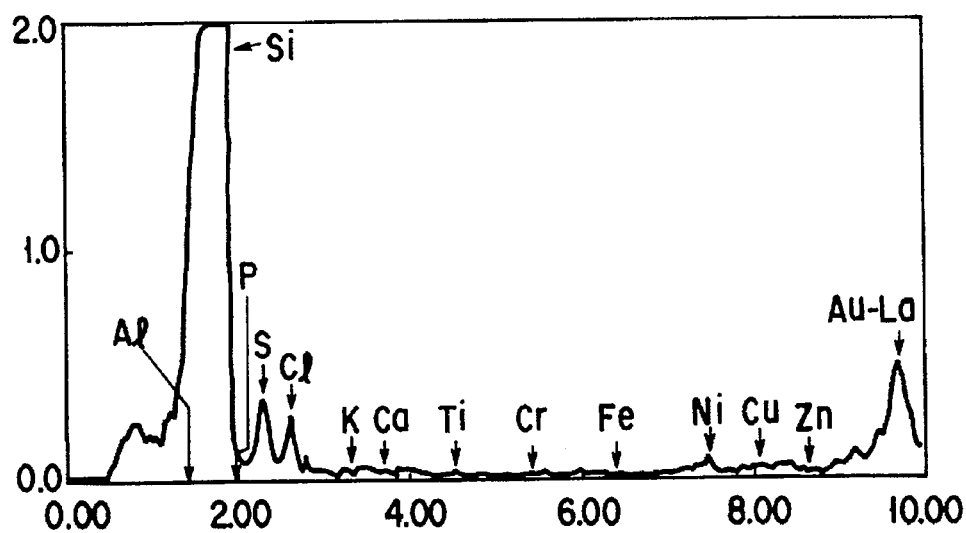
FIG. 3 is a view showing the intensities of different impurities as obtained by the total reflection fluorescent X-ray analysis on a dried solid to which a liquid drop containing very small amounts of impurities is evaporated on a silicon wafer.

One embodiment of the present invention will be explained below with reference to the accompanying drawings.

FIG. 4 is a cross-sectional view showing a sheet 10 as used in the embodiment of the present invention. A thin film layer 12 is covered on the surface of the semiconductor wafer 11 to provide that sheet 10.

The semiconductor wafer 11 is composed of a silicon wafer having a mirror surface of 125 mm in diameter and 1 mm in thickness. The thin film layer 12 is heat-resistant in nature and contains, as a principal component, elements not detected on total reflection fluorescent X-ray analysis. The surface has a total reflection mirror surface and is hydrophobic and acid-resistant. To be specific, an element, such as H, He, Li, Be, B, C, N, O, F and Ne in particular, is used singly or a compound containing the element as a principal component is used, for example, graphite, amorphous carbon or boron nitride, to form the thin film layer, but the layer does not contain any impurity element detected in a very small amount on the total reflection fluorescent X-ray analysis, such as the elements Na to Zn corresponding to the atomic numbers 11 to 30, respectively. The thin film layer 12, being comprised of the amorphous carbon, is 1000 Å in thickness, but the thickness is not restricted thereto. The thin film layer 12 may be set to a thickness with which a total reflection phenomenon occurs. The thin film layer may be formed by a PVD, a CVD or any proper method using heat.

It is to be noted that it is possible to achieve high-sensitivity analysis with the use of an inorganic layer as the thin film layer 12.

A liquid drop 13, containing impurities in very small amounts, is put on the surface of the sheet 10 and has its water content evaporated to a dried solid. An X-ray from an X-ray source 14 is incident on the dried solid on the sheet surface. The dried solid is exposed with an incident X-ray 32 to allow it to be reflected so that the reflected fluorescent X-ray is analyzed on total reflection fluorescent X-ray analysis.

FIG. 5 is a cross-sectional view showing a variant of a sheet used on an apparatus according to another embodiment of the present invention. That sheet 10 per se is formed of the same material as that of which the thin film layer 12 in FIG. 4 is formed. The sheet 10 in FIG. 5 is substantially equal in thickness to the sheet as shown in FIG. 4.

Now, how very small amounts of impurities are analyzed, by the total reflection fluorescent X-ray method, on the sheet 10 in FIG. 4 will be explained below in more detail.

First, explanation will be given below in the case where amorphous carbon is used for the thin film layer 12.

A liquid drop containing metal impurities deposited on the surface of the semiconductor wafer is decomposed with a hydrofluoric acid gas and the surface of the semiconductor wafer is made hydrophobic. Then a diluted hydrofluoric acid drop is scanned as liquid drop on the surface of the semiconductor wafer to collect the metal impurities into the liquid drop. The impurity-collected liquid drop is put on the thin film layer 12 of the sheet 10 in FIG. 4. The thin film layer 12, being hydrophobic, provides a great angle of contact with the liquid drop to enable a corresponding liquid drop to be formed on the thin film layer 12.

The liquid drop thus formed is evaporated to a dried metal impurity solid. An X-ray emergent from the X-ray source 14 is incident to the dried solid at an angle at which a "total reflection" phenomenon occurs, for example, at an angle less than a total reflection critical angle $\phi$ crit. The fluorescent X-ray induced is measured on a total reflection fluorescent X-ray analyzing apparatus, not shown.

A fluorescent X-ray produced from impurities deposited over the thin film layer 12 is detected by a semiconductor detector 40. Upon detection of the fluorescent X-ray, the semiconductor detector 40 outputs an electric signal corresponding thereto, and the electric signal is supplied to a total reflection fluorescent X-ray analyzing apparatus. The total reflection fluorescent X-ray analyzing apparatus is made up of a multichannel analyzer 41 for analyzing outputs detected by the semiconductor detector according to kinds of impurity elements, and data processor 42 for counting outputs produced from the multichannel analyzer. The data processor 42 detects pulses corresponding to the impurity elements and counted within one second, and supplies the resultant detection signal to the computer 43, for quantitative and qualitative analysis of impurities.

In order for the liquid drop to be evaporated to dryness, it is preferred that the surface of the thin film layer 12 be made heat-resistant.

Since, as set out above, the thin film layer 12 is comprised of the heat-resistant layer containing, as a principal component, the element or elements not detected on total reflection fluorescent X-ray analysis, it does not react with the liquid drop so that the surface of the thin film layer 12 is not degenerated. As a result, a requisite flatness is ensured on total reflection fluorescent X-ray analysis and, further, due to better thermal conduction produced in the thin film layer 12, a "dried solid" configuration is better reproduced from the liquid drop.

FIG. 6 shows the intensities of the fluorescent X-ray gained under the total reflection fluorescent X-ray analysis on a dried solid to which a liquid drop containing very small amounts of impurities is evaporated on the sheet surface, the intensities of the fluorescent X-ray differing among these impurities.

As appreciated from FIG. 6, Si (silicon) in the very small amounts of impurities involved can be detected without overlapping with the intensity peaks of the fluorescent X-ray of Al (aluminum) or P (phosphorus) slightly spaced 0.25 KeV or 0.27 KeV apart from an Si energy detection position. In this connection it is to be noted that, in the embodiment shown in FIG. 6, a phosphorus peak has not been confirmed and hence has been found nonexistent as an impurity.

On the sheet 10 of the embodiment shown in FIG. 4, as set out above, even when an X-ray is incident on the thin film layer 12 constituting the base material, no fluorescent X-ray is not produced there and it is, therefore, possible to highly accurately analyze the very small amounts of impurities in the liquid drop involved.

It is, therefore, possible to detect, at a high-sensitivity level, not only Si (silicon) in the very small amount of impurities not heretofore analyzable but also those light elements, for example, Na, Al and P.

Even in the embodiment using the variant of the sheet as shown in FIG. 5, it is possible to obtain the same effect as that gained from the embodiment shown in FIG. 4. Since, in this embodiment, the sheet 10 is comprised of the thin film layer 12 only, the intensity of the Si fluorescent X-ray can be lowered, thus improving analytical sensitivity and accuracy on the apparatus.

In the total reflection fluorescent X-ray analyzing apparatus, the S/N ratio of the fluorescent X-ray intensity detector cannot normally be varied and, if the Si peak as a main peak is suppressed to a lower level, then a whole background is remarkably lowered, thus resulting in lowering a background also in a energy position of any of other elements to be measured in very small amounts. It is, therefore, possible to detect, at a high-sensitivity level, not only Si (silicon) in the elements to be measured in very small amounts but also those light elements emerging in the low energy positions, for example, Na, Al and P.

Even in an energy distributed type semiconductor detector normally used in this way, very small amounts of metal impurities over a range from a low to a high energy can be highly accurately analyzed at high sensitivity.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus used for total reflection fluorescent X-ray analysis on a sample containing very small amounts of impurities, comprising:

a sheet having a hydrophobic and acid resistant surface formed of either one of a single element of Li, Be, and C, and a compound containing H, He, Li, Be, C, N, O, F, or Ne as a principal component and from which the fluorescent X-ray to be detected cannot be obtained when the total reflection fluorescent X-ray is applied to the sheet;

an X-ray source for directing an X-ray as an incident X-ray at the sample on the sheet means and containing such very small amounts of impurities to allow the sample to be analyzed by total reflection fluorescent X-ray analysis;

a fluorescent X-ray detector for detecting fluorescent X-rays produced from the sample; and a fluorescent X-ray analyzer.

2. The apparatus according to claim 1, wherein said sheet has a heat-resistant surface.

3. The apparatus according to claim 1, wherein said sheet is formed of either one of graphite, amorphous carbon and boron nitride.

4. The apparatus according to claim 1, wherein said sheet comprises a sheet and a heat-resistant thin film layer formed on a surface of the sheet and containing, as a main component, an element not detected by the total reflection fluorescent X-ray analysis.

5. The apparatus according to claim 4, wherein said thin film layer has a hydrophobic surface.

6. The apparatus according to claim 4, wherein said thin film layer has an acid-resistant surface.

7. The apparatus according to claim 4, wherein said thin film layer has a heat-resistant surface.

8. The apparatus according to claim 4, wherein said sheet is made of silicon.

9. The apparatus according to claim 4, wherein said thin film layer is formed of either one of a single element of Li, Be, B, and C, and a compound containing H, He, Li, Be, B, C, N, O, F, or Ne as a principal element.

10. The apparatus according to claim 4, wherein said thin film layer is formed either one of graphite, amorphous and boron nitride.

* * * * *

UNITED STATES PATENT AND TRADEMARK OFFICE
CERTIFICATE OF CORRECTION

PATENT NO. : 5,636,256
DATED : June 03, 1997
INVENTOR(S) : Tuyoshi MATUMURA et al.

It is certified that error appears in the above-indentified patent and that said Letters Patent is hereby corrected as shown below:

On Title page, Item [57], in the Abstract, line 6, "x-ray" should read --X-ray--.

Claim 10, column 6, line 52, after "amorphous", insert --carbon--.

Signed and Sealed this

Twenty-fifth Day of November, 1997

Attest:

BRUCE LEHMAN

*Attesting Officer*        *Commissioner of Patents and Trademarks*